United States Patent
Kenneally et al.

(10) Patent No.: US 6,465,642 B1
(45) Date of Patent: *Oct. 15, 2002

(54) LOWER ALKYL ESTER RECYCLING IN POLYOL FATTY ACID POLYESTER SYNTHESIS

(75) Inventors: Corey James Kenneally, Maineville; James Earl Trout, West Chester; Robert Joseph Sarama, Loveland, all of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/797,018

(22) Filed: Feb. 7, 1997

(51) Int. Cl.⁷ .......................... C07H 13/02; C07H 1/00
(52) U.S. Cl. ........................................ 536/119; 536/124
(58) Field of Search .................. 536/124, 119

(56) References Cited

U.S. PATENT DOCUMENTS

| | | | | |
|---|---|---|---|---|
| 2,999,858 A | | 9/1961 | Curtis et al. ................. | 260/234 |
| 3,600,186 A | | 8/1971 | Mattson et al. ................. | 99/1 |
| 3,963,699 A | * | 6/1976 | Rizzi et al. ................. | 536/119 |
| 4,334,061 A | | 6/1982 | Bossier, III ................. | 536/119 |
| 4,517,360 A | * | 5/1985 | Volpenhein ................. | 536/119 |
| 4,518,772 A | | 5/1985 | Volpenhein ................. | 536/119 |
| 4,565,794 A | * | 1/1986 | de Buda ...................... | 502/83 |
| 4,806,632 A | | 2/1989 | McCoy et al. ................. | 536/124 |
| 4,931,552 A | | 6/1990 | Gibson et al. ................. | 536/119 |
| 4,942,228 A | | 7/1990 | Gibson ........................ | 536/119 |
| 5,006,648 A | * | 4/1991 | Van der Plank et al. .... | 536/119 |
| 5,043,438 A | | 8/1991 | Buter ........................ | 536/119 |
| 5,055,571 A | * | 10/1991 | Van Lookeren ............. | 536/124 |
| 5,071,975 A | * | 12/1991 | Van der Plank et al. .... | 536/119 |
| 5,144,023 A | * | 9/1992 | Willemse .................... | 536/124 |
| 5,175,323 A | * | 12/1992 | Cooper ....................... | 554/164 |
| 5,231,199 A | | 7/1993 | Willemse .................... | 554/174 |
| 5,239,097 A | * | 8/1993 | Barkey Wolf et al. ....... | 554/190 |
| 5,250,155 A | * | 10/1993 | Zwanenburg et al. ......... | 203/34 |
| 5,422,131 A | | 6/1995 | Elsen et al. ................. | 426/531 |
| 5,440,027 A | | 8/1995 | Hasenhuettl ................. | 536/115 |
| 5,466,843 A | * | 11/1995 | Cooper ....................... | 554/149 |
| 5,491,226 A | | 2/1996 | Kenneally .................... | 536/115 |
| 5,550,220 A | * | 8/1996 | Meyer et al. .............. | 536/18.5 |
| 5,580,966 A | * | 12/1996 | Buter et al. ................. | 536/18.6 |
| 5,596,085 A | * | 1/1997 | Silver et al. ............... | 536/18.6 |
| 5,648,483 A | * | 7/1997 | Granberg et al. ........... | 536/119 |
| 5,681,948 A | * | 10/1997 | Miller et al. ................. | 536/115 |

FOREIGN PATENT DOCUMENTS

| | | | |
|---|---|---|---|
| EP | 0 233 856 A2 | | 8/1987 |
| EP | 0254376 | * | 1/1988 |
| EP | 0256585 | * | 2/1988 |
| EP | 0 272 759 A2 | | 6/1988 |
| EP | 0301634 | * | 2/1989 |
| EP | 0424066 | * | 4/1991 |
| WO | 9311141 | * | 6/1993 |

* cited by examiner

*Primary Examiner*—Johann Richter
*Assistant Examiner*—L. E. Crane
(74) *Attorney, Agent, or Firm*—Erich D. Hemm

(57) ABSTRACT

Process for synthesizing polyol fatty acid polyesters which includes the steps of reacting an excess of lower alkyl ester with polyol to esterify hydroxyl groups thereof and form polyol fatty acid polyester, separating at least a portion of the unreacted lower alkyl ester from the polyol fatty acid polyester, and recycling the separated unreacted lower alkyl ester for further reaction with polyol or partially esterified polyol. The recycled lower alkyl ester is substantially free of lower alkyl ester degradation reaction products, such as carbonyls and free fatty acids.

7 Claims, No Drawings

LOWER ALKYL ESTER RECYCLING IN POLYOL FATTY ACID POLYESTER SYNTHESIS

TECHNICAL FIELD

This invention relates to a process for synthesizing polyol fatty acids polyesters in which unreacted lower alkyl ester is recovered from the reaction mixture and recycled for use in the polyol fatty acid polyester synthesis. More particularly, this invention relates to such a process wherein good product quality of polyester synthesized with the recycle ester is maintained by minimizing alkyl ester degradation reactions such as oxidation, hydrolysis, pyrolysis, and saponification.

BACKGROUND ART

The food industry has recently focused attention on polyol polyesters for use as low-calorie fats in food products. Triglycerides (triacylglycerols) constitute about 90% of the total fat consumed in the average diet. One method by which the caloric value of edible fat can be lowered is to decrease the amount of triglycerides that is consumed, since the usual edible triglyceride fats are almost completely absorbed in the human system (see *Lipids*, 2, H. J. Deuel, Interscience Publishers, Inc., New York, 1955, page 215). Low calorie fats which can replace triglycerides are described in Mattson, et al., U.S. Pat. No. 3,600,186. Mattson, et al. disclose low calorie, fat-containing food compositions in which at least a portion of the triglyceride content is replaced with a polyol fatty acid polyester having at least four fatty acid ester groups, with each fatty acid having from eight to twenty-two carbon atoms.

Rizzi and Taylor, U.S. Pat. No. 3,963,699, disclose a solvent-free transesterification process in which a mixture of polyol (such as sucrose), a fatty acid lower alkyl ester (such as a fatty acid methyl ester), an alkali metal fatty acid soap (emulsifier), and a basic catalyst is heated to form a homogenous melt. Excess fatty acid lower alkyl ester is added to the melt to form the higher polyol fatty acid polyesters. The polyesters are then separated from the reaction mixture using various separation procedures; distillation or solvent extraction are preferred.

Volpenhein, U.S. Pat. Nos. 4,517,360 and 4,518,772, discloses a solvent-free transesterification process in which a mixture of polyol (such as sucrose), fatty acid ester selected from the group consisting of methyl esters, 2-methoxy ethyl esters, and benzyl esters, an alkali metal fatty acid soap, and a basic catalyst is heated to form a homogenous melt, to which is added excess fatty acid ester to form the higher polyol fatty acid polyesters. The polyesters are then separated from the reaction mixture using various separation procedures; distillation, water washing, conventional refining techniques or solvent extraction are preferred.

Bossier (III) U.S. Pat. No. 4,334,061, discloses a process in which a mixture of polyol, fatty acid ester, alkali metal fatty acid soap, and basic catalyst is heated to form a homogenous melt, to which is added excess fatty acid ester to form the polyol fatty acid polyesters. The polyesters are then recovered by contacting the crude reaction product with an aqueous washing medium while maintaining the resulting mixture at a pH of from 7 to about 12, in the presence of an emulsion decreasing organic solvent. The alkali metal fatty acid soaps and the color-forming bodies are dissolved in the aqueous phase. The polyol fatty acid polyester is recovered from the organic phase by solvent extraction to remove excess fatty acid lower alkyl esters and steam stripping to remove trace amounts of residual fatty acid lower alkyl esters and solvent.

Virtually all of the polyol fatty acid polyester synthesis processes require that the polyol fatty acid polyester be separated from a reaction mixture comprising products, by-products, and unreacted ingredients. Additionally, many polyol polyester synthesis processes require the use of excess lower alkyl ester, in particular excess methyl ester, so that a significant amount of unreacted lower alkyl ester is contained in the reaction mixture from which the polyol polyester product is recovered. The polyol fatty acid polyester synthesis would therefore be more economically efficient if the excess methyl esters could be reused in the polyol fatty acid polyester synthesis. However, because significant degradation of the lower alkyl esters can occur in conventional processing steps employed to separate and purify the polyol polyester product or in separation of the unreacted lower alkyl ester from the reaction mixture, reuse of the degraded lower alkyl ester can result in the synthesis of inferior polyol polyester product. Consequently, there remains a need to develop a process which can recycle the excess lower alkyl ester from a polyol fatty acid polyester synthesis without adversely affecting product quality of polyesters synthesized from the recycled ester.

SUMMARY OF INVENTION

Accordingly, it is an object of this invention to obviate problems encountered in the prior art and provide improved processes for synthesis of polyol fatty acid polyesters.

It is another object of this invention to minimize the side reactions which degrade lower alkyl esters during such processes to allow the recycle of excess lower alkyl ester without adversely impacting the quality of polyol fatty acid polyester produced therefrom.

It is yet another object of this invention to provide a novel process for the production of polyol fatty acid polyesters, which process recycles unreacted ingredients and improves the economics of the polyol synthesis.

It is a related object of this invention to provide a novel process for the production of polyol fatty acid polyesters, which process eliminates the need to dispose of significant amounts of unused excess reactants.

In accordance with one aspect of the present invention, there is provided a novel process for synthesizing polyol fatty acid polyester comprising the steps of reacting lower alkyl ester and polyol, partially esterified polyol or mixtures thereof to esterify hydroxyl groups thereof and form polyol fatty acid polyester comprising partially and/or fully esterified polyol in admixture with unreacted lower alkyl ester; separating at least a portion of the unreacted lower alkyl ester from the polyol fatty acid polyester; and recycling the separated unreacted lower alkyl ester for further reaction with polyol or partially esterified polyol, wherein the recycled lower alkyl ester is substantially free of lower alkyl ester degradation reaction products.

In accordance with another aspect of the present invention there is provided a novel transesterification process for synthesizing polyol fatty acid polyester comprising the steps of heating a mixture of polyol, fatty acid lower alkyl ester, basic reaction catalyst, and optionally an alkali metal fatty acid soap to form a reaction mixture; subsequently adding to the reaction mixture excess fatty acid lower alkyl ester; reacting a portion of said fatty acid lower alkyl ester with polyol to obtain a product mixture; separating unreacted fatty acid lower alkyl ester from the product mixture; and recycling the separated unreacted fatty acid lower alkyl ester for further reaction, wherein the recycled lower alkyl ester is substantially free of degradation reaction products.

It has been found that unreacted lower alkyl esters can be recovered from the product mixture of product, by-products and unreacted ingredients, and recycled for use in the polyol fatty acid polyester synthesis with no adverse impact on the polyol fatty acid polyester reaction or on the quality of the polyester produced. Potential degradation reactions, such as oxidation, hydrolysis, pyrolysis, and saponification, are minimized so as to recycle directly back to the synthesis reactor the unreacted lower alkyl ester which is substantially free of degradation reaction products. The recycling of unreacted lower alkyl esters according to the invention improves the economics of the synthesis reaction, since separated unreacted fatty acid lower alkyl esters which contain high levels of degradation product would need to be further processed to remove substantial amounts of the degradation products from the ester recycle, or otherwise would need to be discarded, either of which can be expensive.

Additionally, it has been found that the same basic compounds which are used to catalyze the polyol fatty acid polyester synthesis can also be used to neutralize fatty acids in the recycled ester, thereby further improving the economical aspects of the synthesis processes employing ester recycle.

These and additional objects and advantages will be more fully apparent in view of the following detailed description.

DETAILED DESCRIPTION OF THE INVENTION

The present invention encompasses processes for recycling lower alkyl esters in the synthesis of polyol fatty acid polyesters. Lower alkyl ester recycling can be used in conjunction with any polyol fatty acid polyester synthesis method which utilizes lower alkyl esters. Such processes are disclosed in U.S. Pat. Nos. 3,963,699; 4,517,360; 4,518,772; 4,806,632 and 5,491,226, incorporated herein by reference. One suitable polyol fatty acid polyester synthesis process is a solvent-free transesterification reaction which can be performed in two steps. In the first step of the transesterification synthesis process, polyol, fatty acid lower alkyl ester, basic reaction catalyst, and optionally soap are combined to form a heterogeneous mixture.

As used herein, the term "polyol" is intended to include any aliphatic or aromatic compound containing at least two free hydroxyl groups. Suitable polyols can be selected from the following classes: saturated and unsaturated straight and branch chain linear aliphatics; saturated and unsaturated cyclic aliphatics, including heterocyclic aliphatics; or mononuclear or polynuclear aromatics, including heterocyclic aromatics. Carbohydrates and non-toxic glycols are preferred polyols. Monosaccharides suitable for use herein include, for example, mannose, glucose, galactose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. Natural sugar alcohols which are suitable for use herein are sorbitol, mannitol, and galactitol. Particularly preferred classes of materials suitable for use herein include the monosaccharides, the disaccharides and sugar alcohols. Preferred polyols include glucose, fructose, glycerol, polyglycerols, sucrose, zylotol, sorbitol, alkoxylated glycerines, alkoxylated polyglycerols, and sugar ethers; particularly preferred is sucrose.

As used herein, the term "polyol fatty acid polyesters" is intended to include fatty acid esters of polyols, in which one or more of the hydroxyl groups are replaced with esters of fatty acids. Preferred polyol fatty acid polyesters are those wherein at least half of the hydroxyl groups have been replaced with esters of fatty acids. Particularly preferred are sucrose polyesters with at least five ester linkages per sucrose molecule, in which the fatty acid chains have from about eight to about twenty-four carbon atoms. As used herein, the term "lower alkyl ester" is intended to include fatty acid esters of lower alkyl alcohols, in which the hydroxyl groups are replaced with esters of fatty acids. Suitable lower alkyl alcohols include C1–C6 monoalcohols. Especially preferred lower alkyl esters are methyl esters.

Suitable fatty acid esters can be derived from either saturated or unsaturated fatty acids. Suitable preferred saturated fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, erythrogenic acids. In a preferred embodiment of the invention, the fatty acid chains have from about two to about twenty-four carbon atoms. Hydrogenated or unhydrogenated lower alkyl esters obtained from soybean oil, palm kernel oil, coconut oil, sunflower oil, safflower oil, corn oil, cottonseed oil, peanut oil, canola oil, high erucic acid rapeseed oil, and mixtures thereof are preferred.

In the present processes, polyol fatty acid polyester is synthesized and unreacted lower alkyl ester is recycled. In particular, a polyol fatty acid polyester is synthesized by a process comprising the steps of (a) reacting lower alkyl ester with polyol, partially esterified polyol, or mixtures thereof to esterify hydroxyl groups thereof and form polyol fatty acid polyester, the polyol fatty acid polyester comprising partially esterified polyol, fully esterified polyol, or mixtures thereof, and being in admixture with unreacted lower alkyl ester, (b) separating at least a portion of the unreacted lower alkyl ester from the polyol fatty acid polyester, and (c) recycling the separated unreacted lower alkyl ester for further reaction with polyol or partially esterified polyol, wherein the lower alkyl ester which is recycled for further reaction is substantially free of lower alkyl ester degradation reaction products. As used herein, "substantially free" of lower alkyl degradation reaction products means that the use of the recycled lower alkyl ester will not adversely effect the quality of the polyol polyester product formed from the recycled lower alkyl ester. Degradation reaction products of the lower alkyl ester will be apparent to those skilled in the art and comprise products of oxidation, hydrolysis, pyrolysis, saponification and the like. These degradation reaction products should be minimized or eliminated to permit direct recycling of the lower alkyl ester to the polyol polyester reaction, without resorting to extra cleanup or purification steps for the recycled esters.

EXCESS METHYL ESTER RECYCLING a) Oxidation

Oxidation of lower alkyl esters can result in the formation of carbonyls and other double-bonded structures, which can directly lead to off-color in the lower alkyl ester material as well as in the polyol polyester product produced therefrom. Oxidation can be minimized or substantially prevented by eliminating exposure of the lower alkyl esters to sources of oxygen (e.g., air) such as by performing the synthesis reaction, separation processing and recycle under a blanket of an inert gas so that the unreacted lower alkyl ester is maintained in the inert gas atmosphere. Suitable inert gases include nitrogen, carbon dioxide and helium. Oxidation can also be minimized by using a vacuum in order to exclude sources of air from synthesis reactions and separation and recycle processes. Further, eliminating or reducing light exposure of the lower alkyl ester reactant and minimizing the trace metal content of the lower alkyl ester and other reactants will also reduce oxidation degradation reactions. The processes according to the present invention are therefore preferably conducted in these manners in order to minimize oxidation reactions whereby the lower alkyl ester which is recycled for further reaction is substantially free of oxidation degradation reaction products. Preferably, the recycled lower alkyl ester has a carbonyl value of less than 200 ppm and a peroxide value of less than about 85 ppm. Additionally, the trace metal content of the alkyl ester is preferably reduced to less than about 0.2 ppm Fe and less than about 0.1 ppm Cu in order to further minimize any oxidative reactions in the alkyl ester reactant which is recycled.

b) Hydrolysis

Hydrolysis reactions are minimized by avoiding or substantially preventing exposure of the unreacted lower alkyl ester to acidic conditions and/or elevated temperatures, for example temperatures greater than about 85° C., particularly in the presence of water, as such exposures lead to the conversion of the fatty acid lower alkyl ester to fatty acid. Free fatty acid is to be avoided in the recycled lower alkyl ester, since it will stoichiometrically be neutralized by, and thereby consume, the basic catalyst used to catalyze the polyol polyester esterification reaction. The neutralization of the free fatty acid by the basic catalyst forms soap. Excessive amounts of soap in the polyol polyester reaction are to be avoided, since they can lead to an increase in viscosity of the polyol polyester reaction mixture. At the later stage of the esterification reaction, it is important to remove by-product methanol from the reaction mixture to drive the reaction toward completion. Inert gas sparging or vacuum are commonly used to carry away methanol that has been formed and which migrates to the liquid-gas interface. Consequently, highly viscous reaction mixtures slow the methanol mass transfer rate and hence, its removal rate from the reaction mixture, thereby directly affecting the reaction rate and degree of completion.

The pH of the polyol fatty acid polyester synthesis reaction preferably is no less than about 7. Preferably any fatty acid which is formed is neutralized. During subsequent steps of refining and finishing of the polyol fatty acid polyester, the pH preferably is no less than 5.5. Using a sufficiently strong base to neutralize any fatty acid present in the recycle ester, without saponifying the alkyl esters to an excessive degree, will minimize any negative effects on the polyol polyester esterification reaction.

Preferably, the hydrolysis reactions are minimized so that the lower alkyl ester is substantially free of fatty acid, whereby direct recycle of the lower alkyl ester to the polyol polyester reaction will not adversely affect the quality of the polyol polyester product formed therefrom. The free fatty acid content of the recycled alkyl ester should be, by weight percent, preferably less than about 0.3, more preferably less than about 0.2, and most preferably less than about 0.1.

Generally, the extent of the hydrolysis reaction which occurs in the lower alkyl ester reactant depends on the level of water present, the temperature of the lower alkyl ester and the contact time with water. As discussed supra, water is used to wash the polyol polyester reaction products of impurities and byproducts, whereby the excess alkyl ester is exposed to the wash water. The usage level of water is selected by color removal requirements, with 2 to 20 percent water by weight of the polyol polyester oil generally being suitable. The temperature of the lower alkyl ester is preferably maintained at less than about 85° C. (185° F.) during water processing, and the contact time of the lower alkyl ester with water is preferably less than about 30 minutes, more preferably less than about 15 minutes, even more preferably less than about 10 minutes, and most preferably less than about 5 minutes. The water can be separated from the reaction product by gravity settling or centrifugation. Gravity settling may require up to about 2 hours. A preferred embodiment uses centrifugation of less than about 10 minutes, preferably less than about 5 minutes.

As discussed above, fatty acid neutralization in the recycle ester is conducted without saponifying the alkyl ester to an excessive degree. The maximum level of saponification products which can be present in the lower alkyl ester recycle is preferably not greater than about 1.0 percent by weight, and more preferably not greater than about 0.5 percent by weight, and even more preferably not greater than about 0.2 percent by weight. Most preferably, the saponification products will be non-detectable; i.e., about 0 percent.

Preferably, the same basic material can be used to both catalyze the polyol fatty acid polyester synthesis reaction and neutralize any fatty acid in the recycled lower alkyl ester. Suitable basic compounds to be used as basic reaction catalysts and as fatty acid neutralizers include alkali metals such as sodium, lithium and potassium; alloys of two or more alkali metals such as sodium-lithium and sodium-potassium alloys; alkali metal hydrides, such as sodium, lithium and potassium hydride; alkali metal lower (C1–C4) alkyls such as butyl-lithium; and alkaline metal alkoxides of lower (C1–C4) alcohols, such as lithium methoxide, potassium t-butoxide, potassium methoxide, and/or sodium methoxide. Other suitable basic compounds include carbonates and bicarbonates of alkali metals or alkaline earth metals. A preferred class of basic catalysts include potassium carbonate, sodium carbonate, barium carbonate, or mixtures of these compounds having particle sizes that are less than about 100 microns, preferably less than about 50 microns. It has been found that when these specific compounds are used as catalysts, increased yields of light-colored higher polyol polyesters are obtained when compared to essentially identical reactions carried out using more conventional catalysts, such as sodium hydride, potassium hydride, soap, or sodium methoxide. These preferred catalysts can be used in admixture with the more conventional basic catalysts, described above. Potassium carbonate and/or potassium methoxide are also preferred catalysts. The use of these catalysts is further disclosed in U.S. Pat. No. 4,517,360 (Volpenhein), which is incorporated by reference.

In a preferred embodiment, the basic compound used as both a basic reaction catalyst and a fatty acid neutralizer is potassium carbonate. For the transesterification reaction, the level of basic catalyst is typically from about 0.01 to about 0.5, preferably from about 0.01 to about 0.1, more preferably from about 0.02 to about 0.05 moles of catalyst per mole polyol. If the basic catalyst is also used to neutralize fatty acids in the recycle ester, the level will be adjusted to an amount effective for neutralizing the acids without excessively saponifying the methyl esters, as discussed above. To minimize saponification of the alkyl esters, the amount of base catalyst which is employed is preferably limited to one to two times the stoichiometric amount of base required to neutralize the free fatty acid content of the lower alkyl ester reactant. Preferably, when the excess lower alkyl ester reactant is recycled for further polyol polyester production, the catalyst level is typically increased, if at all, by an amount of up to about 20% above the level of catalyst employed for production when only fresh lower alkyl ester is employed and no lower alkyl ester is recycled.

c) Pyrolysis

It is also desirable to minimize pyrolysis degradation reaction products in the lower alkyl ester reactant. Generally, pyrolysis of the polyol polyester can occur in evaporation and/or stripping processes which can be used to separate the excess lower alkyl ester reactant from the polyol fatty acid polyester product. Free fatty acid is one of the primary pyrolysis products. If pyrolysis of the polyol polyester occurs, the pyrolysis products are carried off with the lower alkyl ester material during removal. Additionally, pyrolysis generally is a time-dependent reaction. In the production of sucrose polyesters, pyrolysis tends to become significant at approximately 230° C. (450° F.) and becomes instantaneous at approximately 310° C. (590° F.). (On the other hand, the temperature limit for the transesterification reaction is approximately at 149° C. when the polyol is sucrose, owing to carmelization of the sucrose at significantly higher temperatures.) Accordingly, preferred temperature ranges during evaporation and/or stripping of lower alkyl ester from the polyol polyester product are from about 200° C. (400° F.) to 260° C. (500° F.), for sucrose polyester.

Separation of lower alkyl ester from the polyol fatty acid polyester product can be effected with many different reactor designs; batch, continuous, and column reactors, inter alia, can all be utilized. For example, fatty acid methyl esters can be distilled by batch (single stage or multi stage) distillation or by continuous distillation. For batch distillation, residence times typically range from about four hours to about thirty hours, preferably from about six hours to about eighteen hours, more preferably from about eight hours to about twelve hours. For continuous distillation, residence times typically range from about 0.1 to about ten minutes, preferably, from about 0.5 to about 5 minutes. Pressures of from about 0.005 to about 30 mm, preferably from about 1 to about 5 mm, of mercury are used in the distillation process. Temperatures typically range from about 120° C. (250° F.) to about 260° C. (500° F.). The lower alkyl esters can also be recovered from the reaction mixture by solvent extraction, suitably using known techniques, with the provision that the extraction conditions are controlled so as to substantially prevent degradation reactions of the lower alkyl ester as discussed above.

In a preferred embodiment, the lower alkyl esters are removed from the polyol fatty acid polyester product using a two-step process. Generally, the crude polyol fatty acid polyester product will contain from about 20 to about 60 weight percent of the lower alkyl ester, i.e., methyl ester, reactant. In the first step of the preferred separation process, the lower alkyl ester concentration is reduced to a range of from about 0.5 weight percent to about 5 weight percent using an evaporation device, for example, a flash tank, a falling film or rising film evaporator, a wiped film evaporator, any combination thereof, or the like. This step of the separation process is typically limited by heat transfer. The vapor fraction from the vessel is the lower alkyl ester recycle stream. The liquid fraction is the polyol polyester product stream. In the second step of the preferred separation method, the lower alkyl ester concentration in the polyol fatty acid polyester product stream is further reduced from the about 0.5 weight percent to about 5 weight percent content resulting from the evaporation step, to less than about 0.1 weight percent using a multi-stage mass transfer device, for example, packed columns or tray columns, together with gas stripping. Steam or nitrogen can suitably be employed as the stripping gas. The second step of the separation process is typically limited by mass transfer. The process conditions for the evaporation and stripping steps are controlled in order to avoid degradation reactions of the sucrose polyester as discussed above. Preferably, the evaporation and stripping processes are conducted at temperatures of from about 190° C. to about 260° C., more preferably from about 200° C. to about 230° C. and even more preferably, from about 215° C. to about 225° C., and at pressures of from about 0.1 to 10 mm Hg, more preferably from about 0.5 to about 5 mm Hg, and even more preferably from about 0.5 to about 1.0 mm Hg.

TRANSESTERIFICATION

Transesterification reactions used to produce polyol fatty acid polyesters can optionally include a soap as an emulsifier. Suitable soaps include alkali metal fatty acids soaps. As used herein, the term "alkali metal fatty acid soaps" is intended to include the alkali metal salts of saturated or unsaturated fatty acids having from about eight to twenty-four carbon atoms, preferably from about eight to about eighteen carbon atoms. Accordingly, suitable alkali metal fatty acid soaps include, for example, lithium, sodium, potassium, rubidium, and cesium salts of the fatty acids described herein. Mixtures of fatty acids derived from one or more of soybean oil, sunflower oil, safflower oil, cottonseed oil, palm oil and corn oil are preferred. Accordingly, preferred alkali metal fatty acid soaps include, for example, the potassium soap made from soybean oil fatty acids.

The absolute level of soap is desirably kept low; but should be at least enough to dissolve the polyol at an acceptable rate. Therefore, the level of soap can be reduced as a result of using smaller particle polyol and/or reaction conditions that favor the solubilizing of the polyol. The level of soap in the first stage of the transesterification is typically from about 0.001 to about 0.75, preferably from about 0.1 to about 0.5, moles of soap per mole of polyol. The soap is preferably used in combination with another emulsifier, preferably with the lower esters of the polyol and the fatty acid which are present either by being added as part of the initial reaction mixture, or by back-mixing. Preferred lower polyol polyesters are sucrose lower polyesters having no more than about 5 esters per molecule sucrose. The soap is preferably potassium soap of hydrogenated fatty acids containing from about eight to about twenty-four carbon atoms. The use of such soaps is further disclosed in U.S. Pat. No. 5,491,226 (Kenneally) which is incorporated by reference.

If soap is used as an emulsifier, after the average degree of esterification reaches about 60%, the soap emulsifier is no longer needed to facilitate the reaction and, therefore, can be removed. The soap emulsifier is not essential after the polyol has reacted once and there is sufficient partial ester to maintain homogeneity of the reaction mixture. Removal of soap can be accomplished by known techniques, e.g., by filtration, centrifugation, etc., since the soap is relatively insoluble in the reaction mixture at high degrees of esterification. The filtered reaction mixture typically has a soap level of less than about 0.5 moles of soap per mole polyol, preferably less than about 0.05 moles of soap per mole polyol. On a weight basis, about 0.5 moles of soap per mole polyol is generally from about 4% to about 10% soap, by weight of the mixture, and about 0.05 moles of soap per mole polyol is generally from about 0.4 to about 1% soap, by weight of the mixture; one of ordinary skill will appreciate that the weight percent value is dependent on the levels of soap and polyol in the mixture. The soap material removed from the reaction mixture by filtration can be recycled for use as a reactant in the first step reaction mixture.

As used herein, all ratios are molar ratios unless otherwise specified, and all percentages are by weight unless otherwise specified. In general, the heterogeneous mixture comprises from about 5% to about 25%, preferably from about 10% to about 20%, by weight of the polyol; from about 70% to about 92%, preferably from about 75% to about 85%, by weight of the fatty acid esters; from about 1% to about 30%, preferably from about 2% to about 10%, by weight of the alkali metal fatty acid soap; and from about 0.01% to about 5%, preferably from about 0.01% to about 0.5%, more preferably from about 0.05% to about 0.3%, by weight of the basic catalyst. The ratio of the fatty acid chains of the lower alkyl ester to the hydroxyl groups of the polyol is typically in the range of about 0.5:1 to about 1.5:1. The ratio of catalyst to polyol typically ranges from about 0.02:1 to about 0.2:1.

The heterogeneous mixture is heated to a temperature of from about 60° C. (140° F.) to about 180° C. (356° F.), preferably from about 110° C. (230° F.) to about (293° F.), more preferably from about 130° C. (260° F.) to 135° C. (275° F.), under pres from about 0.01 to about 2500 mm Hg, preferably from about 0.01 to about 1500 mm Hg. A homogeneous melt of partially esterified polyols (lower polyesters) and unreacted starting materials will form in from about one to about four hours. As used herein, the term "lower polyesters" are those esters of the polyol wherein up to about 50% of the hydroxy groups of polyol have been esterified. In the case of sucrose, the primary sucrose fatty acid lower esters are mono, di, and/or tri-esters.

In the second step of the transesterification process, excess fatty acid lower alkyl ester is added to the homogeneous melt formed in the first step. As used herein, the term "excess" is intended to be an amount beyond that required to form lower polyol fatty acid polyesters. When fatty acid methyl esters are used, it is preferred that after the excess esters are added to the reaction mixture, the mixture is heated to a temperature of from about 120° C. (248° F.) to about 160° C. (320° F.), preferably at about 135° C. (275 pressure from about 0.01 to about 2500 mm Hg, preferably from about 0.1 to about 1500 mm Hg. The reaction time for the second step is preferably less than about 10 hours, and generally is between about 2 to about 8 hours. During the second step, the partially esterified polyol is further esterified to provide highly esterified polyol fatty acid polyesters. As used herein, the term "highly esterified polyol fatty acid polyester" refers to a polyol wherein at least about 50%, preferably at least about 70%, and most preferably at least about 96%, of the hydroxy groups are esterified. In the case of highly esterified sucrose polyesters, this typically refers to the hexa-, hepta-, and particularly octa-esters.

The transesterification reaction can be conducted in any of the reactors conventionally employed, including, but not limited to batch, semi-batch and continuous reactors. Column reactors, packed or multi-stage, are suitable for use in the transesterification reaction. Plug flow column reactors are particularly preferred.

As the transesterification reaction proceeds, a lower alcohol is formed as a by-product. In order to promote the reaction, the alcohol by-product is preferably removed. Many removal techniques are known in the art and can be used to effectively and efficiently remove the lower alkyl alcohol. Vacuum removal, with and without an inert gas sparging, can be used to promote the reaction. Alternatively, inert gas sparging can be used at atmospheric or greater pressures to promote methanol and other alcohol removal.

The use of specific catalysts and soap:polyol ratios permit the combination of steps 1 and 2 into a single reaction step. The use of such catalysts is further disclosed in U.S. Pat. No. 4,517,360 (Volpenhein), and the use of such soap:polyol ratios is further disclosed in U.S. Pat. No. 4,518,772 (Volpenhein), both references incorporated herein by reference. In this single step approach, a mixture of a polyol, alkali metal fatty acid soap, basic catalyst selected from potassium carbonate, sodium carbonate, barium carbonate and mixtures thereof and excess fatty acid lower alkyl ester is heated to a temperature from about 100° C. (212° F.) to about 180° C. (356° F.) at a pressure from about 0.1 to about 760 mm of mercury. The soap:polyol molar ratio is from about 0.6:1 to about 1.1, preferably from about 0.75:1 to about 1.1, more preferably from about 0.75:1 to about 0.85:1, most preferably about 0.75:1. In the final step of the transesterification process, the polyol fatty acid polyesters are separated from the reaction mixture containing polyesters, by-products, and unreacted starting materials. Separation can be accomplished with any of the separation procedures routinely used in the art. Distillation, water washing, and conventional refining techniques or solvent extractions are preferred, with the provision that the steps noted above be taken to prevent substantial degradation of lower alkyl ester which is to be recycled. In the final step, the unreacted fatty acid lower alkyl esters recovered from the reaction mixture are recycled, for use as ingredients in the first and second steps of the transesterification process.

The processes of the present invention are further understood in view of the following examples in which all parts and percentages are by weight, unless otherwise specified.

EXAMPLE 1

This example describes a pilot plant two stage process for synthesizing polyol fatty acid polyesters wherein methyl ester reactant was separated and recycled for further reaction. The polyol fatty acid polyester product comprised sucrose fatty acid polyester (SPE). The methyl ester comprised about 80% soybean methyl ester having about 12% C16 alkyl methyl ester, about 87% C18 alkyl methyl ester, and about 1% other methyl esters; and about 20% cottonseed methyl ester having about 23% C16 alkyl methyl ester, about 76% C18 alkyl methyl ester, and about 1% other methyl esters. One batch of liquid SPE was made using only fresh methyl ester reactant as a control, while six subsequent batches were made using a blend of fresh esters and recycle esters from the previous batch. Each batch employed 36% by weight excess esters. Owing to various process losses, only 22 weight percent of the total ester used was separated and recycled for use in the subsequent batch. All of the lower alkyl ester which was separated and recycled was employed in the first stage of the two-stage transesterification reaction.

In the first stage of each batch, 350 lbs. sucrose, 200 lbs. potassium stearate, 1,530 lbs. methyl ester and 2.8 lbs. potassium carbonate catalyst were charged to a stirred tank reactor, and maintained at a temperature of from about 132° C. to 138° C. and a pressure of from about 1 to about 10 mm Hg. The batch process used a single reactor comprising a tank with an agitator and a recirculation pump. There are two impellers on the agitator; one pitched blade (for solids suspension) and one Rushton turbine (for gas dispersion). A four stage vacuum system capable of pulling 1.0 mm Hg was used to remove methanol by-product from the reactor. Nitrogen sparging was used as a stripping agent to assist in methanol removal. In the second stage of the transesterification reaction, an additional 1,830 lbs. methyl ester and 2.8 lbs. potassium carbonate catalyst were added. Total residence time to achieve 75% octaester was from about 6 to about 10 hours.

The polyol fatty acid polyester product was centrifuged, water washed and bleached with silica gel for refinement. Centrifugation was performed with a disc stack centrifuge; about 95% of the emulsifier (potassium stearate soap) was removed from the crude (unrefined) polyol polyester. Water-washing was done in a stirred tank; the water level was about 18% by weight of the crude polyol polyester, the mixing time was from about 10 to about 30 minutes. The water phase was separated by gravity settling. The crude polyol polyester was then dried to a moisture content of less than about 0.1% in a vacuum dryer. Silica gel bleaching was performed by contacting dry silica with the crude polyol polyester in a stirred tank for 30 minutes; the silica level was about 1% by weight of the crude polyol polyester. The silica gel was separated from the polyol polyester in a filter press. For all six processing batches, the batch reaction time, the soap level after centrifuging and the soap level after water washing were consistent.

The methyl ester was separated from the bleached polyester product using evaporation and stripping processes. The evaporation was performed with a wiped film design evaporator operating under a pressure of about 1.0 mm Hg and a temperature of about 425° F. (about 218° C.). The methyl ester which was vaporized and recondensed in the evaporator was recycled. Steam stripping of the polyol polyester completed the methyl ester removal. Steam stripping was performed with a packed column with countercurrent flow of steam and polyol polyester operating under a pressure of about 4.0 mm Hg and a temperature of about 425° F. (about 218° C.).

The methyl ester which was separated for recycle from each batch of liquid SPE exhibited measurements within the acceptable limits for peroxide value, percent free fatty acid, chain length distribution and visual appearance. Results for peroxide value, carbonyl value, percentage of free fatty acid, and chain length distribution are set forth in Table 1.

One method of determining peroxide value is thiosulfate titration. Peroxides reduce the KI to $I_2$, and $I_2$ can complex with starch indicator to create a blue color. A thiosulfate titrant oxides the $I_2$, causing the blue color to disappear; 0.5 mole of $I_2$ is consumed per mole thiosulfate.

A potassium iodide solution of 15 grams KI in 10 ml deionized water and a 0.01N thiosulfate solution were prepared. Samples were prepared by dissolving 20 grams of sample with 30 ml of a 60:40 v:v glacial acetic acid/1,1,2-trichlorotrifluoroethane solution, adding 1 ml of the KI solution, agitating for 1 minute, adding 100 ml of distilled water, mixing, and adding 2 ml of a starch indicator solution (Fisher Scientific, #SS408-1). The samples were then titrated with the thiosulfate to a colorless endpoint.

The peroxide value was calculated using the equation:

$$\text{ppm } H_2O_2 = \frac{(34 \text{ g/mole } H_2O_2)(\text{moles thiosulfate titrant})}{(0.5 \text{ thio}/I_2)(10^6 \text{ ppm/g})}{\text{sample weight (g)}}.$$

Preferably, the peroxide value is less than about 85 ppm.

One method of determining free fatty acid level is with phenolphthalein titration. One milliliter of phenolphthalein indicator, 50±0.2 grams of sample and 100 ml of warm neutral denatured alcohol were mixed. The solution was titrated to a phenolphthalein endpoint using 0.01N NaOH. The percent free fatty acid (%FFA) was reported as % oleic acid, and was calculated according to the equation:

$$\%\text{FFA as Oleic} = \frac{[(\text{ml of NaOH}) \times (\text{Normality of NaOH}) \times 28.21]}{\text{Sample Weight}}.$$

Preferably, the percentage of free fatty acid is less than about 0.4%, more preferably less than about 0.3%.

One method of determining fatty acid chain length distribution is by gas chromatography. Fatty acid lower alkyl esters can be separated by gas chromatography by chain length. Samples were dissolved in hexane and analyzed on a capillary GC having a 50 m×0.22 id fused column (Supelco SP-2340). The column head pressure was 25 psi, the helium carrier gas flowrate was 2–3 ml/minute, the split vent flow rate was 100 ml/minute, the initial temperature in 175° C., the final temperature was 195° C., the rate was 1.6° C./minute, the air pressure was 40 psi, the air flowrate was 400 ml/minute, the hydrogen pressure was 30 psi, and the hydrogen flowrate was 30 ml/minute. Preferably, chain length distribution remains consistent throughout the recycling; i.e. the chain length varies from the chain length of fresh methyl ester by no more than about 20%, preferably no more than about 15%. Most preferably the chain length for C16 lower alkyl ester varies no more than about 15%, and the chain length for the C18 lower alkyl ester varies no more than about 5%. For soybean methyl ester, the chain length generally comprises from about 8% to about 14% C16 lower alkyl ester, and about 85% to about 95% C18 lower alkyl ester. For cottonseed methyl ester, the chain length generally comprises from about 19% to about 23% C16 lower alkyl ester, and from about 74% to about 84% C18 lower alkyl ester.

One method of determining carbonyl value is based upon reacting fatty acid lower alkyl ester with an ethanolic solution of 2,4-dinitrophenylhydrazine (2,4-DNPH) and hydrochloric acid to form 2,4-dinitrophenylhydrazones, which in the presence of a base produce red color. A 2,4-DNPH stock solution was prepared by dissolving 0.8±0.02 g of 2,4-DNPH in 200 ml of 200 proof (100%) undenaturated ethanol, and then adding 10 ml of concentrated HCl. A KOH solution was prepared by dissolving 118 g of KOH in 500 ml of distilled water, and diluting to 2000 ml with 200 proof undenaturated ethanol. A dodecanal stock solution was prepared by diluting 0.200±0.001 g of odecanal to 50 ml with 200 proof undenaturated ethanol. The carbonyl concentration was calculated as:

$$\text{ppm } C=O = \frac{\text{ug } C=O \text{ in stock}}{\text{ml}}$$

-continued $$= \frac{\text{weight of dodecanal (g)}}{50 \text{ ml}} \times \frac{28}{184} \times F \times \frac{10^6}{\text{g}} \frac{\text{ug}}{};$$

F=% purity of dodecanal/100.

The dodecanal stock was diluted 50-fold with 200 proof undenatured ethanol to form a working solution; the working solution was used to make calibration standards. Fatty acid lower alkyl ester samples were prepared by diluting 0.1±0.0100 g of sample with 4 ml of ethanol.

Each of the samples, standards, and ethanol blanks was placed in a 25-ml volumetric flask, and 2 ml of the 2,4-DNPH solution was added to each flask. Stoppered flasks were placed in a 75±1° C. water bath for 20±0.5 minutes, cooled to room temperature, diluted to 25 ml with the KOH solution, and mixed well with shaking. After standing at room temperature for 20±0.5 minutes, the absorbance was read at 480 nm using quartz cells. A calibration curve was constructed from the absorbance values of the calibration standards. Preferably, the carbonyl value is less than 200 ppm.

The level of soap remaining in the polyol polyester reaction product after centrifuging is preferably less than 2000ppm. One method of determining the level of soap is by acid tritiation. Samples were prepared by mixing 0.5±0.01 grams of sample with 50 ml of a 1:1 v:v isopropanol/deionized water solution. The sample was titrated with 0.01N HCl using an automatic titrator. One equivalence point was observed.

$$\% \text{ K soap} = \frac{(\text{ml HCl})(\text{Normality HCl}) \times 32.0^{**}}{\text{sample weight}}$$

**32.0 = Molecular Weight K soap (g/mol) * 0.001 1/ml * 100

TABLE 1

Comparison of Fresh and Recycled Methyl Ester

| Methyl Ester | Peroxide Value (ppm) | Carbonyl Value (ppm) | % Free Fatty Acid | % C16 Chain Length | % variation from fresh | % C18 Chain Length | % variation from fresh |
|---|---|---|---|---|---|---|---|
| Acceptable Limits | <85 | <200 | <0.4 | 10.6 to 16.2 | +/−20 | 80 to 89.8 | +/−20 |
| Fresh | 3.2 | 91.6 | 0.03 | 14.1 | | 84.88 | |
| Recycled | | | | | | | |
| Batch 1 | 16.1 | 67.1 | 0.15 | 14.6 | 3.5 | 84.6 | 3.3 |
| Batch 2 | 4.1 | 53.7 | 0.19 | 13.66 | 3.1 | 85.52 | 0.8 |
| Batch 3 | 9.5 | 70.4 | 0.23 | 13.42 | 4.8 | 85.9 | 1.2 |
| Batch 4 | 3.5 | 62.4 | 0.20 | 13.59 | 3.6 | 85.54 | 0.8 |
| Batch 5 | 3.1 | 64.5 | 0.20 | 13.3 | 5.7 | 85.99 | 1.3 |
| Batch 6 | 8.4 | 67.3 | 0.21 | 13.62 | 3.4 | 85.54 | 0.8 |

The liquid SPE products made from fresh methyl ester and from five batches of recycled methyl ester had values within the acceptable limits for percent octaester, flavor, color and residual soap after centrifuging. Results for percentage octaester, color and residual soap after centrifuging are set forth in Table 2.

One method of determining the percent of octaester in a polyol polyester is with high performance liquid chromatography. The polyol polyester sample was dissolved in hexane, filtered, and injected into the HPLC where normal phase separation based on the number of free hydroxyl groups takes place. A 80 mm by 4 mm, 5 μm Zorbax Reliance silica column was used. The mobile phase is a methyl-t-butyl/hexane step gradient system. The gradient consists of 4.8 minutes of 4% methyl-t-butyl in hexane; 2.9 minutes of 16% methyl-t-butyl in hexane; 1.9 minutes of 25% methyl-t-butyl in hexane; 1.9 minutes of 50% methyl-t-butyl in hexane; and 2.9 minutes of 100% methyl-t-butyl in hexane. Detection was by a light-scattering mass detector. The octaester level was calculated by the integrator as the normalized octaester area percent. Preferably, the octaester level is greater than about 70%.

Color was determined using a Lovibond Automatic Tintometer with a red/yellow calibration standard (2.9 red/12.0 yellow). The color was reported in AOCS red and yellow units. Preferably, the color is less than about 3.7 Lovibond red units.

TABLE 2

Comparison of Sucrose Polyester Quality Using Fresh and Recycled Methyl Ester Substrate

| Methyl Ester Substrate | % Octaester | Residual Soap After Centrifuging (ppm) | Final Color (Lovibond Red) |
|---|---|---|---|
| Acceptable Limits | >70 | <2000 | <3.7 |
| Fresh | 79.3 | 587 | 2.4 |
| Recycled | | | |
| Batch 1 | 75.2 | 1117 | 2.7 |
| Batch 2 | 78.1 | 1128 | 2.9 |
| Batch 3 | 78 | 890 | 2.5 |
| Batch 4 | 78.1 | 584 | 2.7 |
| Batch 5 | 78.3 | 817 | 2.4 |

One of ordinary skill will appreciate that other analytical methods may be employed to determine peroxide value, carbonyl value, percentage of free fatty acids, chain length distribution, color, octaester content, and residual soap level.

EXAMPLE 2

This example describes a production process for synthesizing sucrose fatty acid polyesters (SPE) with the use of recycle methyl esters in a two step continuous process. The methyl ester comprised cottonseed methyl ester of about 23% C16 alkyl methyl ester, about 76% C18 alkyl methyl ester, and about 1% other methyl esters. In the first stage, the continuous reaction system was made up with 267 lb/hr sucrose, 60 lb/hr potassium stearate, 1,116 lb/hr methyl ester and 9 lb/hr potassium carbonate. The second stage was made up with 1,560 lb/hr methyl ester and 6 lb/hr potassium carbonate. A series of continuous stirred tank reactors (CSTRs) were used for the continuous reaction system; each reactor comprised a tank with an agitator and a recirculation pump. There were two impellers on the agitator; one pitched blade (for solids suspension) and one Rushton turbine (for gas dispersion). The overall process ran for approximately 100 hours, with unreacted methyl ester being recycled for additional reaction after the first 24 hours of the process. The weight percentage of recycle esters was the same as in Example 1 and all of the recycled esters were employed as the methyl ester in the first stage. A four stage vacuum system capable of pulling 1.0 mm Hg was used to remove methanol by-product from the reactor. Nitrogen sparging was used as a stripping agent to assist in methanol removal.

The polyol fatty acid polyester product was centrifuged, water washed and bleached with silica gel for refinement. Centrifugation was performed with a disc stack centrifuge; about 95% of the emulsifier (potassium stearate soap) was removed from the crude (unrefined) polyol polyester. Water-washing was done in an agitated tray column; the water level was about 18% by weight of the crude polyol polyester, the mixing time was from about 2 to about 10 minutes. The water phase was separated by centrifugation. The crude polyol polyester was then dried to a moisture content of less than about 0.1% in a vacuum dryer. Silica gel bleaching was performed by contacting dry silica with the crude polyol polyester in a stirred tank for 30 minutes; the silica level was about 0.5% by weight of the crude polyol polyester. The silica gel was separated from the polyol polyester in a filter press. The in-process measurements, including reactor residence time, soap level after centrifuging and soap level after water washing, were also consistent during the entire production run.

The methyl ester was separated using evaporation and stripping processes. The evaporation was performed with a wiped film design evaporator operating under a pressure of about 1.0 mm Hg and a temperature of about 425° F. (about 218° C.). The methyl ester which was vaporized and recondensed in the evaporator was recycled. Steam stripping of the polyol polyester completed the methyl ester removal. Steam stripping was performed with a packed column with countercurrent flow of steam and polyol polyester operating under a pressure of about 4.0 mm Hg and a temperature of about 425° F. (about 218° C.).

The peroxide value, carbonyl value, percentage of free fatty acids, chain length distribution and visual appearance for the recycle ester were within acceptable limits during the entire production run. Results for peroxide value, carbonyl value, percentage of free fatty acid, and chain length distribution are set forth in Table 3. Additionally, percent of SPE octaester, flavor, color and residual soap after centrifuging for the liquid SPE product were within acceptable limits during the entire production run. Results for percentage octaester, color and residual soap after centrifuging are set forth in Table 4. The analytical measurements were performed as discussed in Example 1.

TABLE 3

Comparison of Fresh and Recycled Methyl Ester

| Methyl Ester | Peroxide Value (ppm) | Carbonyl Value (ppm) | % Free Fatty Acid | % C16 Chain Length | % variation from fresh | % C18 Chain Length | % variation from fresh |
|---|---|---|---|---|---|---|---|
| Acceptable Limits | <85 | <200 | <0.4 | 19 to 27 | +/− 20 | 60 to 79 | +/− 20 |
| Fresh(Day 1) | 10 | 196 | 0.04 | 22.5 | | 75.5 | |
| Recycled | | | | | | | |
| Day 2 | 15.2 | 102 | 0.11 | N.A. | N.A. | N.A. | N.A. |
| Day 3 | 20 | 122 | 0.11 | 21.5 | 4.7 | 76.5 | 1.3 |
| Day 4 | 14.8 | 100 | 0.12 | 20.9 | 7.1 | 77.1 | 2.1 |
| Day 5 | 14 | 128 | 0.12 | 19.3 | 14.2 | 78.7 | 4.2 |

N.A. = Not Available

TABLE 4

Comparison of Sucrose Polyester
Quality Using Fresh and Recycled Methyl Ester Substrate

| Methyl Ester Substrate | % Octaester | Residual Soap After Centrifuging (ppm) | Final Color (Lovibond Red) |
|---|---|---|---|
| Acceptable Limits | >70 | <2000 | <3.7 |
| Fresh (Day 1) | 76 | 483 | 1.7 |
| Recycled | | | |
| Day 2 | 78 | 900 | 1.1 |
| Day 3 | 77 | 600 | 1.5 |
| Day 4 | 75 | 600 | 1 |
| Day 5 | 76 | 400 | 1.5 |

Having described the preferred embodiments of the present invention, further adaptations of the processes described herein can be accomplished by appropriate modifications by one of ordinary skill in the art without departing from the scope of the present invention. A number of alternatives and modifications have been described herein, and others will be apparent to those skilled in the art. Accordingly, the scope of the present invention should be considered in terms of the following claims, and is understood not to be limited to the details of the processes described in the specification.

What is claimed is:

1. An esterification and separation process for synthesizing polyol fatty acid polyesters, which process minimizes degradation reaction products in unreacted lower alkyl esters during synthesis of the polyol fatty acid polyesters, the process comprising the steps of:

(a) reacting lower alkyl ester with polyol, partially esterified polyol, or mixtures thereof to esterify hydroxyl groups thereof and form polyol fatty acid polyester, said polyol fatty acid polyester comprising partially esterified polyol, fully esterified polyol, or mixtures thereof, the polyol fatty acid polyester being in admixture with unreacted lower alkyl ester to obtain a product mixture, wherein the reaction of said lower alkyl ester, said partially esterified polyol, or said mixtures thereof occurs in the presence of from about 0.001 moles to about 0.7 moles of soap per mole of polyol;

(b) removing residual soap from the product mixture of step (a);

(c) water-washing and drying the product mixture to remove impurities; wherein the water-washing temperature is less than about 85° C., and the unreacted lower alkyl ester has a contact time with water of less than about 15 minutes;

(d) bleaching the product mixture for refinement;

(e) separating at least a portion of the unreacted lower alkyl ester from the polyol fatty acid polyester in the product mixture, wherein the separated unreacted lower alkyl ester is free of degradation reaction products;

(f) recycling the separated unreacted lower alkyl ester directly back to step (a) for further reaction with polyol, partially esterified polyol, or mixtures thereof; and wherein said process is solvent-free.

2. A process according to claim 1, wherein the separated unreacted lower alkyl ester has a carbonyl value of less than about 200 ppm.

3. A process according to claim 1, wherein the separated unreacted lower alkyl ester has a peroxide value of less than about 85 ppm.

4. A process according to claim 1, wherein the separated unreacted lower alkyl ester comprises less than about 0.3 weight percent free fatty acid.

5. A process according to claim 1, wherein the separated unreacted lower alkyl ester comprises less than about 1.0 weight percent saponification products.

6. A process according to claim 1, wherein the unreacted lower alkyl ester is separated from polyol fatty acid polyester by evaporating the unreacted lower alkyl ester at a temperature of from about 190° C. to about 260° C., at which temperature the degradation reaction of the polyol fatty acid polyester is prevented.

7. A process according to claim 1, comprising the step of refining the polyol fatty acid polyester in the presence of a base selected from the group consisting of alkali metals, alloys of 2 or more alkali metals, alkali metal hydrides, C1–C4 alkali metal lower alkyls, alkaline metal alkoxides of C1–C4 alcohols, carbonates and bicarbonates of alkali metals or alkaline earth metals and mixtures thereof wherein the base is included in an amount which is one to two times the stoichiometric amount of base required to neutralize the free fatty acid content of the lower alkyl ester reactant without saponing the lower alkyl esters.

* * * * *